United States Patent [19]

Shamma et al.

[11] 4,087,426

[45] May 2, 1978

[54] OXYBISBERBERINE AND A PROCESS FOR ITS PRODUCTION

[75] Inventors: Maurice Shamma; Jerome L. Moniot, both of State College, Pa.

[73] Assignee: Research Corporation, New York, N.Y.

[21] Appl. No.: 714,531

[22] Filed: Aug. 16, 1976

[51] Int. Cl.² .............................................. C07D 519/00
[52] U.S. Cl. ........................ 260/286 R; 260/287 CF; 260/287; 260/287 D; 260/289 C
[58] Field of Search ........................ 260/289 C, 286 R

[56] References Cited

U.S. PATENT DOCUMENTS

| 3,272,707 | 9/1966 | Tedeschi | 260/289 C |
| 3,426,027 | 2/1969 | Muller | 260/289 C |
| 3,920,665 | 11/1975 | Shimada et al. | 260/289 C |

OTHER PUBLICATIONS

Shamma, "The Isoquinoline Alkaloids", (1972) pg.285, Academic Press.

Primary Examiner—Donald G. Daus
Assistant Examiner—David E. Wheeler
Attorney, Agent, or Firm—Omri M. Behr

[57] ABSTRACT

Berberine and protoberberine analogs thereof are oxidatively dimerized in the presence of a base. Treatment of the dimer with alkanolic anhydrous acid yields the corresponding 8-alkoxyberberine (or protoberberine) phenol betaine which, in turn, may be converted to alpha and beta hydrastine.

7 Claims, No Drawings

OXYBISBERBERINE AND A PROCESS FOR ITS PRODUCTION

BACKGROUND OF THE INVENTION

Berberine is a very readily available alkaloid originally isolated in 1826. The chemistry of berberine is well known (see M. Shamma, The Isoquinoline Alkaloids, Academic Press (1972) pp. 284 – 292).

Heretofore it had been believed that oxidation with ferricyanide yielded the 8-oxyberberine. It is the surprising finding of the present invention that this belief was erroneous.

The oxidative transformation which occurs, and the compounds derived therefrom, are entirely unknown heretofore except that certain of these compounds may be converted into the known beta hydrastine which, in the form of its hydrochloride salt, is used for the treatment of uterine hemorrhageas. (Merck Index, 8th Ed., p. 539, 1968)

SUMMARY OF THE INVENTION

Berberine and its protoberberine analogs (1) are oxidatively dimerized suitably by ferricyanide or ferric ions in the presence of strong inorganic base to form oxybisberberine and analogs thereof (2). Treatment of oxybisberberine with anhydrous alkanolic mineral acid, suitably hydrochloric acid, yields the corresponding 8-alkoxyberberine (or protoberberine) phenol betaine (3) which, in turn, is hydrolytically cleaved to yield dehydronorhydrastine alkyl ester (4). Alkylation to the corresponding N-alkyl analog (5), followed by reductive lactone formation, yields a mixture of alpha (6a) and beta (6b) hydrastine and the corresponding analogs thereof. These compounds are useful in the treatment of hemorragheas.

Treatment of the oxidation dimer (2) with mild organic base and the corresponding hydrochloride salt yields an unisolated intermediate (7) which, in the presence of aqueous acid, yields the corresponding 14-hydroxy-8,13-dioxo compound (8) which may be converted reversibly into the corresponding 14-alkoxy-8,13-dioxo compound (9). Where the dimer is oxybisberberine (9) may be converted in two steps to 13-methoxyoxyberberine (10) which possesses anti-neoplastic activity (Sawa and Ikegawa Jap. Pat. No. 75 19795). Compound (9) may also be obtained directly from intermediate (7) by treatment with anhydrous alkanolic acid. Further, compounds (2) and (3) may be directly converted into compound (10) by treatment with an appropriate alkylating agent.

FLOW SHEET I

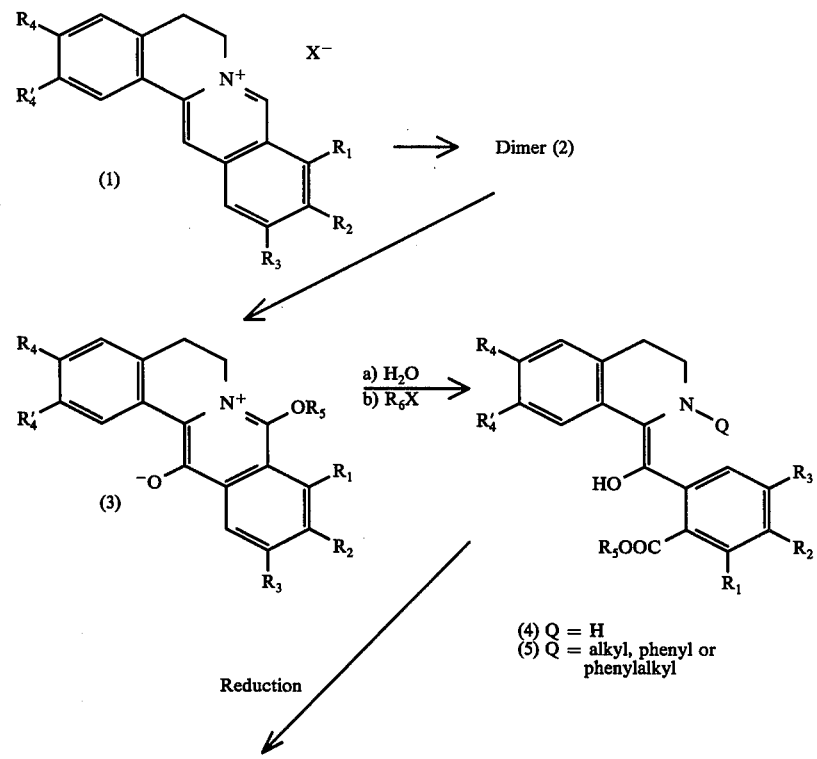

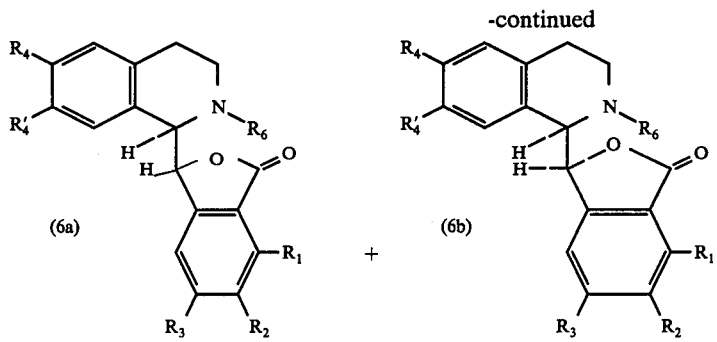

(6a) + (6b)

FLOW SHEET II

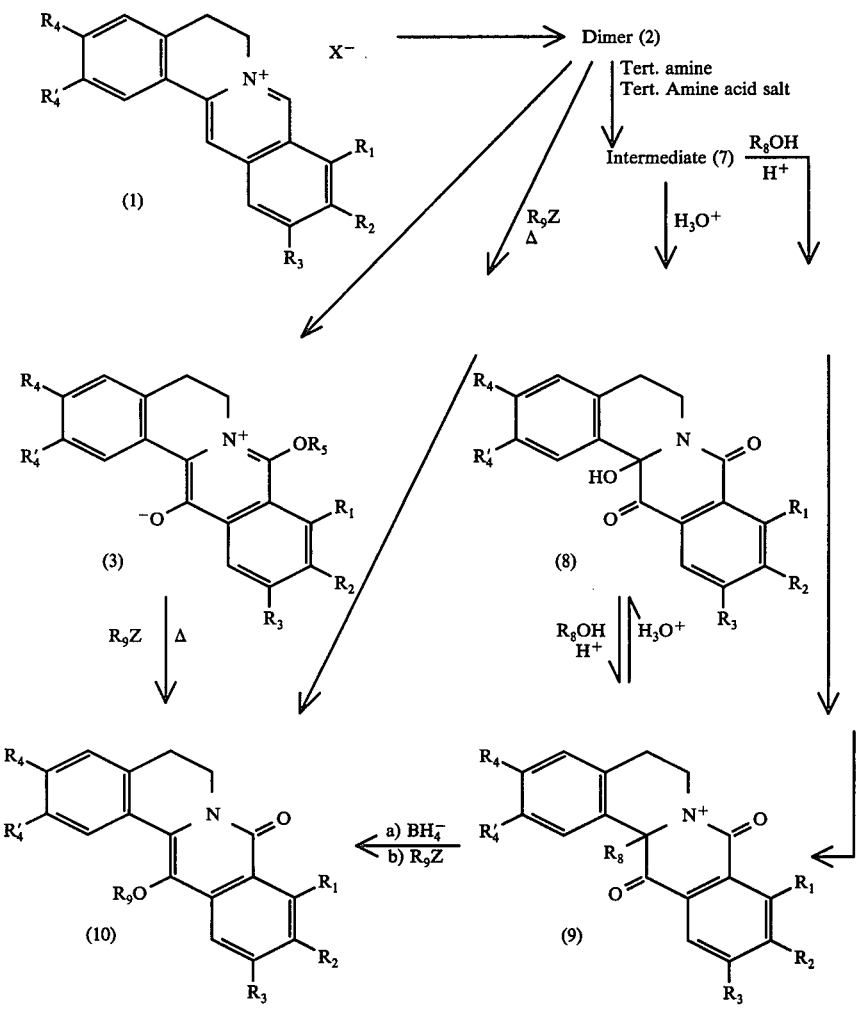

DESCRIPTION OF THE PREFERRED EMBODIMENTS

The reaction sequence for the oxidative dimerization of berberine and certain protoberberine analogs, and the subsequent conversion thereof to alpha and beta hydrastine and their analogs, is set forth in the preceding flow sheet (I).

In the foregoing flow sheet, it should be recognized that the reaction sequence set forth can be carried out not only on berberine chloride itself, — that is to say, where $R_1$ and $R_2$ are methoxy, and $R_4$ and $R_4'$ when taken together are methylenedioxy and $X^-$ is chloro, but also on berberine and protoberberine analogs where there are phenolic groups on two of the positions 9, 10, and 11 in the starting materials, and said groups may be either in the free phenolic form or protected by any of the known, stable, phenol protecting moieties as will be set forth in greater detail hereinbelow. Furthermore, the phenolic groups at the 2 and 3 positions may be protected by any of the known phenolic protecting groups both cyclic and acyclic again as set forth hereinbelow.

It should further be noted that the phenolic groups present at either 9, 10 or 10, 11 may also, if desired, be protected by the said cyclic protecting moieties. While this modification is not discussed in detail hereinbelow, it should be considered as following within the scope of the present invention.

In the definitions following, the presence of the prefix "alk" indicates a moiety consisting of 1 to 5 carbon atoms in straight or branch chain orientation except when said term appears as cycloalkyl in which event the term cycloalkyl designates a cyclic moiety containing 3 to 7 carbon atoms in the ring. $R_1$, $R_2$, and $R_3$, when not hydrogen, may be hydroxy, alkanoyloxy, suitably lower alkanoyloxy such as acetoxy, propionoxy, valeroxy, or the like; alkoxy, such as methoxy, ethoxy, propoxy, isopropoxy, butoxy, pentoxy, or the like; phenylalkanoyloxy, suitably phenyl lower alkanoyloxy, such as benzoyloxy, phenylacetoxy, phenylpropionoxy, 2-phenylpropionoxy, phenylvaleroxy, or the like; phenylalkoxy, for example, benzoxy, phenylethoxy, phenylbutoxy, phenylpentoxy, or the like; alkoxyalkoxy, for example, methoxymethoxy, ethoxymethoxy, propoxymethoxy, ethoxypropoxy, propoxybutoxy, methoxybutoxy, propoxypentoxy, and the like; cycloalkylalkoxy, for example, cyclopropylmethoxy, cyclobutylmethoxy, cyclopentylmethoxy, cyclohexylethoxy, cycloheptylbutoxy, and the like; alkoxycarbonyloxy, for example, ethoxycarbonyloxy, propoxycarbonyloxy, butoxycarbonyloxy, or the like; phenylalkoxycarbonyloxy, for example, benzyloxycarbonyloxy, phenylethoxycarbonyloxy, phenylpropoxycarbonyloxy, and the like.

$R_4$ and $R_4'$ have the same values as $R_1$, $R_2$, and $R_3$ other than hydrogen and hydroxy. Furthermore, when joined together, they form difunctional derivatives such as alkylenedioxy, for example, methylenedioxy, ethylenedioxy, 1,3-propylenedioxy, 1,2-propylenedioxy, 1,2-butylenedioxy, 1,4-butylenedioxy, and the like; alkylenedicarbonyloxy, for example, oxalyl, malonyl, succinyl, and the like; phenylalkylenedicarbonyloxy, for example, alphacarboxybenzoyl, 2-phenylsuccinyl, and the like; diphenylalkylenedicarbonyloxy, for example, 2,3-diphenylsuccinyl, and the like; phenylalkylenedioxy, such as 1-phenylethylenedioxy and the like, diphenylalkylenedioxy, for example, 1,2-diphenylethylenedioxy, 1,2-diphenylpropylene-1,3-dioxy, and the like; alkoxyalkylenedioxy, for example, methoxymethylenedioxy, propoxymethylenedioxy, cycloalkylalkylenedioxy, for example, cyclopropylmethylenedioxy, and the like; alkylenedioxydicarbonyloxy, for example, ethylenedioxydicarbonyloxy; phenylalkylenedioxydicarbonyloxy, for example 1-phenylethylenedioxydicarbonyloxy; diphenylalkylenedioxydicarbonyloxy, for example 1,2-diphenylethylenedioxydicarbonyloxy. The foregoing list of substituent groups should be considered as merely illustrative and not limiting.

In those cases where either $R_1$ and $R_2$ are other than hydrogen or hydroxy, or $R_2$ and $R_3$ are other than hydrogen or hydroxy, they may have the same values as $R_4$ and $R_4'$ taken together, but said values need not be identical to the values of $R_4$ and $R_4'$ taken together in that molecule.

$R_5$ is alkyl, suitably lower alkyl — for example, methyl, ethyl, propyl, isopropyl, isobutyl, amyl, and the like — most suitably methyl or ethyl.

$R_6$ has the same value as $R_5$ and additionally may be phenyl or phenylalkyl, suitably phenyl lower alkyl such as benzyl, phenethyl, phenylpropyl, phenylbutyl, or the like — most suitably, lower alkyl such as methyl or ethyl, benzyl and phenyl. Also included in the scope of the moiety is trifluoromethyl.

$X^-$ is an anion of an organic or an inorganic acid. While the invention is not limited thereto, $X^-$ is preferably an ion generated from a readily available quaternizing agent, and, thus, will generally be a halide ion suitably chloride, bromide, or iodide, a nitrate, or a sulfate ion. Among the more readily available organic acid anions may be included the acetate ion, the succinate ion, and the oxalate ion.

The basic feature of the oxidative dimerization step is that the starting material is treated with a mild oxidizing agent prior to the addition of a moderately strong base and the reaction product rapidly removed from the aqueous phase so that further reaction does not take place.

In the preferred procedures, the starting material (1) is prepared as an aqueous solution, preferably a saturated solution, at a temperature within the liquid range of water — that is to say, for a practical point of view from 2° C to 98° C. Nevertheless, it has been found especially convenient to carry out the reaction between 50° C and 70° C suitably at about 60° C. To this solution is added the oxidizing agent suitably in powdered form, the oxidizing agent may be a ferricyanide, suitably an alkali metal ferricyanide such as potassium ferricyanide or sodium ferricyanide, or ammonium ferricyanide; ferric ions generated, for example, by ferric chloride or ferric nitrate may also be employed.

The starting material in this step, when the ultimate product is intended to be β-hydrastine, is the berberinium cation in conjunction with any of the anions as set forth above, suitably chloride, bromide, iodide, nitrate, sulfate or hydrogen sulfate, acetate, or oxalate, although, of course, the invention is not limited thereto. Where it is desired to carry out the process on readily available analogs of berberine, there may be employed other quaternary protoberberinium salts such as the quaternary salts of norcoralydinium, 9-acylberberubinium — for example, the 9-acetylberberubinium the 9-alkylberberubinium — for example, 9-methylberberubinium, palmatinium cations, or 9-acylpalmatrubinium cations.

The mixture of the quaternary salt in aqueous suspension with the oxidizing agent is very stable. When the oxidizing agent is added to the solution of the quaternary salt, a slurry is obtained. This slurry may be held without noticeable deterioration for at least five days if necessary. Longer periods may well be acceptable.

After standing for any suitable time, the supernatant liquid over the slurry is decanted off and discarded. There is then added a concentrated aqueous solution of strong base — suitably, a solution of an inorganic hydroxide most preferably, a saturated solution of an alkali metal hydroxide, an alkali earth metal hydroxide, or ammonium hydroxide. An excess amount of base is required; however, the amount of excess is not critical. Sufficient base is added to insure a permanent color change from a greenish-yellow to a yellowish-tan. The temperature of the reaction is not critical, but, since the reaction is believed to be substantially instantaneous, it is suitably carried out at ambient temperature.

It has been observed, however, that the yields in the reaction decrease substantially where the base remains in contact with the reaction product for periods in excess of thirty minutes. It is, therefore, desirable to commence extraction of the product from the reactant mixture less than ten minutes after addition of the base is complete. Suitably, extraction should be commenced between two and six minutes after addition of the base, and completed within twenty minutes of addition of the base.

The extraction may be carried out by any substantially water immiscible organic solvent. It is preferred to use a solvent which is moderately polar and which, moreover, has a low tendency to form emulsions with aqueous bases. It has been found, as a matter of practicality, that diethyl ether is substantially preferred as the extractant, although the invention is by no means limited thereto. After the initial extraction, the aqueous layer is clarified, suitably by settlement or centrifugation, to remove any emulsified layers, and the organic solvent layer is rapidly filtered through an anhydrous mild inorganic base, suitably through anhydrous potassium carbonate. Rapid handling in this matter is desirable since the dimeric product commences to autocrystallize from the solvent without cooling or concentration after a fairly short time period. The clarified aqueous layer is re-extracted, the solvent similarly filtered and dried, and combined with the first organic extract. The combined solvents are set aside at ambient temperature. Crystallization is complete in approximately two days. The crystals are then separated, suitably by filtration, and purified in the usual manner.

The residual mother liquors from the initial crystallization are concentrated and acidified to recover unreacted starting material.

The thus obtained oxidation dimer is then converted into the corresponding 8-alkoxyberberine or protoberberine phenolbetaine (3). In this procedure, a slurry is prepared of the dimer in a predetermined alkanolic solvent. Preferably there is employed a lower alkanol — for example, methanol, ethanol, isopropanol, n-propanol, n-butanol, isobutanol, or pentanol. This slurry is then treated with anhydrous acid, most suitably, the acid is an acid such as hydrochloric or hydrobromic acid. Most suitably, there is prepared an alkanolic solution of the anhydrous acids utilizing the same alkanol wherein the dimer is slurry. The reaction can be carried out at any liquid temperature of the solvent; however, since the reaction is very rapid, ambient temperature is considered most suitable.

There is added an amount of alkanoic acid containing at least three moles of acid per mole of dimer; however, the use of excess acid is beneficial and in no way harmful. Upon addition, a red color develops substantially immediately and, upon standing, a yellow crystalline mass is precipitated.

The reaction mixture contains both the desired product and a fairly substantial amount of the starting material (1). The separation is carried out in the following manner. The reaction mixture is made basic by the addition of sufficient amount of moderately strong inorganic base to make the reaction mixture just alkaline. Ammonium hydroxide, suitably 2% aqueous ammonium hydroxide, is especially suitable. The reaction mixture is then immediately partitioned between a suitable, moderately polar, substantially water immiscible organic solvent, suitably a reaction inert organic solvent such as ether.

The ether layer is then dried, suitably with an anhydrous inorganic mild base, suitably anhydrous potassium carbonate, and the solvent removed, suitably under reduced pressure. The thus obtained 8-methoxyberberine or protoberberine phenol betaine (3) may then be recrystallized; however, the free base is very susceptible to hydrolysis in the presence of moisture, light, and air. It is therefore desirable to convert it, when storage is desired, in the usual manner, to an acid salt. This may be readily done either by taking up the free base in an anhydrous alkanol, suitably methanol, and adding thereto an alkanolic solution of an anhydrous acid, or by preparing an ethereal solution of the free base and adding anhydrous acid, suitably gaseous anhydrous acid thereto. Any readily available acid may be used — for example, hydrochloric, hydrobromic, hydriodic, nitric, sulfuric, acetic, or perchloric acid. Salts of (3) may also be prepared by admixture of a solution of (3) in a reaction inert organic solvent, suitably a polar water immiscible solvent such as a halogenated hydrocarbon, suitably chloroform, and saturated ethereal solutions of organic acids such as oxalic, maleic, malonic, substituted malonic acids, and the like. It should be noted that the yield in this reaction based on starting material (i.e., berberine) charged is about 50%. The remaining material, however, is not lost, but is recovered in the form of the starting material (1) which can then be readily recycled to the oxidation dimer.

In the reaction sequence, where the betaine (3) is not to be stored, but converted to compound 4 — namely, dehydronorhydrastinemethyl ester and the analogs thereof — the betaine is not converted into acid salt, but utilized as an ether solution. It is preferred to utilize substantially reaction inert solvents, such as diethyl ether, dioxane, tetrahydrofuran. The ether solution is then stirred with water at a pH of between 6 and 8 for from about 48 to about 72 hours. The pH range is important for good yield. The betaine is stabilitized by acid and no hydration will occur at a pH lower than 6; on the other hand, under basic conditions, the hydration reaction proceeds too far and cleavage and decomposition result. A pH in the neighborhood of 7 is, therefore, most desirable. The hydration reaction can take place at any temperature of the liquid range of the solvent. It is, however, adequate, and convenient, to carry out the reaction at ambient temperatures. Completion of the reaction is noted when the initial orange-yellow color of the solution disappears. The ethereal solution is dried in the usual manner and concentrated to small volume. The free base formed in this reaction is unstable in alkali and only moderately stable in a neutral media. The acid salt, however, is stable, and may be prepared suitably from an anhydrous acid in the usual manner. For example, the hydrochloride may be readily prepared by passing anhydrous hydrogen chloride gas through the concentrated ethereal solution.

The dehydronorhydrastine ester is then alkylated at the nitrogen on the isoquinoline ring. As in the previous reaction, the starting material, in this case compound (4), is stabilized as the acid salt. Thus, where the free base has not immediately previously been formed, it is regenerated in the usual manner by slurry in water, neutralization with a mild base, for example, sodium bicarbonate, extraction with a highly polar reaction inert water immiscible solvent such as chloroform, the solution dried in the usual manner, suitably over anhydrous sodium sulfate, and evaporated, under reduced pressure, to an oil. This oil is then taken up in a suitable solvent. There are a number of solvents which are suitable as media for N-alkylation. These solvents are usually water miscible, di-polar organic solvents such as acetone, dimethylformamide, tetrahydrofuran, dimethoxyethane, dioxane, and acetonitrile, of which the last is the most suitable.

The alkylation may be carried out by any suitable alkylating agent. The agent selected would, of course, depend upon the ultimate product desired. Thus, where hydrastine itself is the ultimate product, a methylating agent would be employed; thus, a methyl halide, such as methyl chloride, methyl bromide, or methyl iodide may be used, the last being especially preferred. Other readily available methylating agents such as dimethyl sulfate, trimethyloxonium fluoroborate, or trimethyl phosphate may also be used. Where it is desired to prepare the N-alkyl analogs of hydrastine where the alkyl group is other than methyl, other commonly utilized alkylating agents may be employed; thus, there may be used lower alkyl halides such as ethyl, iodide, n-propyliodide, n-butyliodide, and the like, or, where the alkylating group is phenylalkyl or substituted phenylalkyl, there may be employed, for example, benzyl iodide, phenethyl iodide, phenylpropyl iodide, or the like.

The alkylating agent is added to the solution of (4) in the solvent. It is preferred to utilize a substantial excess of alkylating agent. Suitably, a 3 to 5 molar excess is employed. While the reaction is operative at any temperature range in the liquid phase of the solvents, reaction at lower or ambient temperatures is unacceptably slow. It is, therefore, preferred, although not essential, to carry out the reaction at the reflux temperature of the solvent. The reaction time will vary in accordance with the alkylating agent employed; however, a reaction time of between 3 to 12 hours — suitably 4 to 8 hours — is usually sufficient. While the invention is not limited thereto, it has been found suitable to mix the reactants in the ratio of 100 mg of (4) to 10 ml of solvent to 1 ml of alkylating agent.

Upon completion of the reaction under reflux, the reaction is cooled and the solvent removed, suitably under reduced pressure, to yield a crystalline mass. This crystalline mass is then evaporated and recrystallized, suitably from a mixed solvent such as methanol/ether to give the appropriate quaternary salt (5). This may be further purified in the usual manner.

The quaternary salt is then rearranged to form alpha and beta hydrastine, and the corresponding analogs thereof depending upon the initial starting material employed.

The starting material (5) in the form of the quaternary salt is then taken up in a suitable solvent and rearranged by reduction. The preferred solvent may be a lower alkanol such as ethanol or methanol, a polar ether such as tetrahydrofuran or dioxane, or a base such as pyridine or the like. Anhydrous conditions are not essential. Any of these solvents may be mixed with water in order to aid solvation. The reduction may be carried out either catalytically using hydrogenation in the presence of a noble metal catalyst such as platinum or palladium, or with a mild chemical reducing agent such as sodium borohydride or lithium borohydride, sodium borohydride being especially preferred. The reduction may be carried out at any temperature in the liquid range of the solvent; however, ambient temperature has been found suitable and is preferred. The reaction theoretically requires 0.5 moles of sodium borohydride per mole of the quaternary salt; however, it has been found preferable to utilize an excess of the reducing agent, suitably a 4 to 6 fold excess to give the desired result.

The reaction is fairly rapid, and results in decolorization of the solution. After decolorization is noted, the solution is agitated at ambient temperature, suitably from about 3 to about 6 hours — 4 hours being considered as sufficient.

The reaction mixture is then quenched, suitably by the addition of sufficient aqueous acid — for example, aqueous hydrochloric acid — to make the reaction mixture mildly acidic, and the quenched mixture is permitted to stand suitably for about 2 to about 5 hours — preferably for about 3 hours — to insure completion of the quenching and lactonization.

The quenched solution is then neutralized with a very mild base — suitably with solid sodium bicarbonate — and then extracted. It is preferred to utilize a strong substantially water immiscible reaction inert organic solvent, a halogenated hydrocarbon solvent such as chloroform has been found especially suitable. The chloroform extracts are then dried, suitably over anhydrous sodium sulfate, and evaporated to yield a residue which is then recrystallized — suitably from a lower alkanol, preferably methanol. The resulting crystalline product is a mixture of alpha and beta hydrastine and/or the corresponding analogs thereof, depending upon the starting material utilized. The compounds are then resolved suitably by column chromatography on silica gel, eluting with chloroform/methanol mixtures.

The conversion sequence of the oxidation dimer (2) by various routes to 13-methoxyoxyberbine (10) and its analogs is set forth in flow sheet II. $R_1$, $R_2$, $R_3$, $R_4$, and $R_5$ have the same values as discussed and set forth hereinabove. $Rk_8$ is selected from the same group of values as $R_5$ and $R_9$ is selected from the same group of values as $R_6$. Z is any suitable group attached to the alkyl moiety of an alkylating agent — for example, halide such as iodide or bromide, sulfate, phosphate, or oxoniumfluoroborate.

In the preparation of unisolated intermediate (red filtrate) (7), the oxidation dimer (2) — for example, oxybisberberine or any of the other analogs thereof set forth herein — is taken up in a tertiary amine. The amine may be a tertiary alkyl amine such as trimethylamine or triethylamine, or an aromatic tertiary amine such as pyridine or ring substituted pyridines — for example, picolines, lutidines, or collidine or the like. The solution is then treated with an excess of a mineral acid salt of the tertiary amine. Any mineral acid salt may be utilized — for example, the hydrogen chloride, the hydrogen sulfate, the hydrobromide, or the like — the hydrogen chloride being generally employed because of convenience of availability. There is utilized approximately two parts by weight of the hydrochloride salt per part by weight of the dimer (2); however, the use of a larger amount of amine salt does not interfere with the reaction. The reaction is preferably carried out between 0° C and approximately 30° C — preferably at about 20° C. At the lower end of the temperature range, reaction is very slow and at temperatures in the neighborhood of 70° C the entire ring system breaks up.

The solution is stirred for from about 2 to about 4 hours, and allowed to settle. A crystalline precipitate of the appropriate acid salt of the starting matrial (1) precipitates out in crystalline form. The reaction mixture — that is to say, the filtrate from the crystallization (red filtrate) (7) should be worked up promptly after crystallization to obtain better yield of compounds (8) or (9).

In the conversion of intermediate (7) to the corresponding 8,13-dioxo-14-hydroxyberbine or analog thereof (8) the reaction mixture in the previous step is filtered, and poured onto a mixture of ice and moderately strong mineral acid. Any mineral acid is operative; however, hydrochloric acid of between 10 and 30, suitably about 20% per weight is preferred. The reaction mixture from the previous step has a red color. Upon contact with the cold acid, a violet-black color results together with the formation of a copious precipitate. Thereupon, sufficient water should immediately be added to affect a decolorization of the reaction mixture. If isolation of compound (8) is desired, it is important that at this stage of the reaction, no other nucleophile be added thereto. The reaction mixture is then promptly extracted with a suitable reaction inert water immiscible organic solvent — suitably a halogenated hydrocarbon such as chloroform. The organic layer is then dried, suitably over anhydrous potassium carbonate or the like, the solvent removed and the residue purified, suitably by column chromatography.

Where it is desired to convert compound (8) to compound (9), compound (8) is taken up in aqueous mineral acid, and the appropriate nucleophile added thereto. This nucleophile may be an alkanol, suitably a lower alkanol such as methanol, ethanol, propanol, butanol, isoamyl alcohol or the like. It may be a carboxylic acid, suitably an alkanoic acid such as acetic acid, propionic acid, butyric acid or the like, or a mercaptan, suitably an alkylmercaptan such as ethylmercaptan, methylmercaptan, butylmercaptan, or the like. This list of nucleophiles is intended to be purely exemplary and in no way limiting.

Upon addition of the nucleophile, the product is worked up as before by extraction with a suitable solvent and isolation from the solvent.

Compound (9) may be obtained directly from intermediate (7). In this procedure the intermediate solution (red filtrate) is diluted with the desired nucleophile — suitably one of the nucleophiles mentioned directly hereinabove, and the solvent removed under reduced pressure. This evaporation is carried out suitably at slightly elevated temperatures — for example, between 30° and 50° C. It has been found desirable to add two further aliquots of the nucleophile, and reevaporate them in the same manner. The resultant residue is then purified, suitably by column chromatography — for example, over silica gel — and then crystallized.

Conversion of compound (9) to the corresponding 13-alkoxy-8-oxoberberine is brought about by sequential reduction and alkylation.

The reaction is carried out in two steps. Compound (9) is reduced — suitably by reaction with a mild reducing agent such as sodium borohydride or lithium borohydride, of which an excess is employed — by taking up Compound (9) in an alkanolic solvent — suitably methanol — and stirring for from about 8 to about 18 hours at from about 10° to about 50° C — suitably at about 20° C. The solvent is then removed, suitably under reduced pressure, the reaction mixture quenched with water at about pH 7, and extracted with a suitable water immiscible inert polar solvent — suitably an halogenated hydrocarbon solvent such as chloroform. The solvent layer is then separated, and dried, suitably over anhydrous potassium carbonate. The solvent is then removed, suitably under reduced pressure, and the residue taken up in pure dry reaction inert polar solent, suitably an ethereal solvent such as ether, tetrahydrofuran, or dioxane. It is preferable to use freshly distilled tetrahydrofuran. To this solution is added the desired alkylating agent — suitably methyliodide, and a strong base such as sodium hydride and the reaction mixture heated, preferably under reflux, for from about 30 minutes to about 2 hours — suitably for about 1 hour, permitted to stand at ambient temperature for between 8 and 18 hours, suitably for about 12 hours, and then quenched by pouring into aqueous mineral acid and extracted and worked up in the usual manner.

General notation: Hereinbelow all temperatures are in ° C and all proportions (i.e., %) are weight/weight.

EXAMPLE I

CONVERSION OF BERBERINE CHLORIDE (1) INTO OXYBISBERBERINE (2)

A saturated solution of berberine chloride (1) (200 g, 0.54 m) in water at 60° C, was treated with powdered potassium ferricyanide until precipitation was complete. The resultant slurry was allowed to stand at room temperature, and the supernatent liquid was decanted. The remaining thick greenish-yellow slurry was treated with an aqueous saturated solution of sodium hydroxide until a permanent color change in the slurry to yellow-tan had occurred. After stirring for two to six minutes, the slurry was rapidly extracted with ether. Both layers clarified, and the organic ether layer was filtered rapidly through anhydrous potassium carbonate, and oxybisberberine (2) allowed to crystallize at room temperature. Crystallization was complete in 48 hours.

Following the collection of the crystals of (2), the ether mother liquors were concentrated and acidified to recover unreacted berberine.

The crystals of (2) were washed successively with water, methanol and ether, and then air dried at room temperature. Recrystallization from pyridine-ether (1:2) afforded (2) as fine white plates, mp 215°–216° C. in 60% yield.

Typical combustion analytical values for oxybisberberine (2) are: C,66.13 ± 0.21; H,55.15±0.25; N, 3.90±0.10 and residual oxygen. The compound shows no carbonyl absorption in its infra-red spectrum. NMR (60 MHz in pyridine-$d_5$) δ(TMS) 2.00–3.40 m (8H) 3.47 (s) (3H); 3.57 s (3H); 3.88 s (3H); 3.93 s (3H); 4.58 m (1H); 5.28 s (1H); 5.60 s (2H); 5.67 m (1H); 5.75 m ABq (2H); 6.27, 6.44, 6.48, 6.58, 6.63, and 6.78: (8H in all); 7.68 s (1H).

Oxybisberberine crystallizes from pyridine-ether as monoclinic plates, mp. 215°–216° dec., in the space group $P2_1/c$ with cell dimensions a = 16.12, b = 11.19, c = 16.91, and β = 118°05'.

In accordance with the above procedures, but starting, in place of berberinium chloride, with norcoralydinium (i.e., 2,3,10,11-tetramethoxyprotoberberinium) chloride, palmatinium (i.e., 2,3,9,10-tetramethoxyprotoberberinium) bromide, berberubinium (i.e., 2,3-methylenedioxy-9-hydroxy-10-methoxyprotoberberinium) chloride, 2,3,10-trimethoxy-11-hydroxyprotoberberinium chloride, 9-acetoxy-2,3,10-trimethoxyprotoberberinium chloride, 11-methoxypalmatinium chloride, or berberubinium 9-carbonic acid ethyl ester (i.e., 2,3-methylenedioxy-9-ethoxycarbonyloxy-10-methoxyprotoberberinium) chloride, there is obtained the corresponding oxidation dimer (2).

EXAMPLE II

CONVERSION OF OXYBISBERBERINE (2) INTO 8-METHOXYBERBERINE PHENOL BETAINE (3) AND ITS HYDROCHLORIDE

A slurry of oxybisberberine (2) (0.5 g, 0.7 mmol) in methanol (50 ml) was treated with 10% methanolic anhydrous hydrogen chloride (20 ml) at ca. 20° C. A red color developed immediately, and upon standing a yellow crystalline mass formed. The entire reaction mixture was partitioned between ether and 2% aqueous ammonia (100 ml), and the organic layer separated and filtered through anhydrous potassium carbonate. Residual emulsions were further extracted with chloroform.

The organic layers were combined, the solvent removed under reduced pressure, and the residue crystallized upon addition of chloroform/ether to give 0.25 g (0.7 mmol) of 8-methoxyberberine phenol betaine (3) as fine orange needles, mp. (free base) 175°–176° C, mp. (hydrochloride, from methanol) 211°–213° C. Anal. Free base (3). Found: C, 65.92; H, 5.02. Calcd. for $C_{21}H_{19}NO_6$: C, 66.14; H, 4.99%. The free base (3) exhibited λmax (in EtOH) 230, 262sh, 313, 359, 374, 455 nm (log ε 4.50, 4.11, 4.09, 3.81, 3.80 and 3.83). The uv absorption pattern did not change upon addition of base. λ max (in EtOH.HCl) 232, 262, 290, 338, 348 and 426 nm. ν max (in disc) 1610, 1500, 1480, 1370, 1300, 1275, 1085, and 1040 $cm^{-1}$. NMR, free base, in $CDCl_3$ solution, 60 MHz, δ 2.90 (t, 2H), 3.86 (s, 3H), 3.98 (s, 6H), 4.58 (t 2H), 5.86 (s, 2H), 6.51 (s, 1H), 7.35 (d, 1H), 8.28 (d, 1H), and 8.80 (s, 1H).

The alkaline aqueous layer was reacidified and extracted with ether to yield berberine chloride (1) (0.2 g 0.54 mmol).

In accordance with the above procedure, but where, in place of methanol (per se and with the acid), there is utilized ethanol, propanol, butanol or amyl alcohol, there was obtained the corresponding 8-ethoxy, 8-propoxy, 8-butoxy and 8-amyloxy berberine phenol betaines (3).

In accordance with the above procedure, but starting with, in place of oxybisberberine, oxybisnorcoralydine, oxybispalmatine, oxybisberberubine and oxybis(2,3,10-trimethoxy-11-hydroxyprotoberberine) produced in accordance with Example I, there is obtained the corresponding 8-alkoxynorcoralydine phenol betaine, 8-alkoxypalmatine phenol betaine, 8-alkoxyberberubine phenol betaine, and 8-alkoxy-2,3,10-trimethoxyprotoberberine phenol betaine.

EXAMPLE III

HYDRATION OF 8-METHOXYBERBERINE PHENOL BETAINE (3) TO DEHYDRONORHYDRASTINE METHYL ESTER (4) HYDROCHLORIDE SALT

A 5 l. saturated ether solution of 8-methoxyberberine phenol betaine (3) was allowed to stir at ca 20° C with 10 ml of water at pH 7 for 48 to 72 hours until the yellow orange color disappeared. The ether solution was dried over anhydrous potassium carbonate, concentrated to a small volume, and dry anhydrous chloride gas passed through. The precipitated hydrochloride salt (85%) was filtered and recrystallized from methanol-ether as light yellow plates mp. 144°–145° C (MeOH-ether), Anal. Found C, 53.73; H,4.67. Calc'd. for $C_{21}H_{21}NO_7.HCl.CH_3OH$: C, 53.90; 4.73%. The uv spectrum of the free base exhibited λmax (in EtOH) 210, 228 and 308 nm (log ε 4.50, 4.37, 4.20 and 4.19). NMR (free base (4) δ 2.73 and 3.81 (2t, 2×2H, $CH_2$—$CH_2$), 3.84, 3.92 and 3.96 (3s, 3×3H, 3 $OCH_3$), 5.98 (s, 2H, $OCH_2O$), 6.70 and 7.03 (2s, 2×1H, C-5 and C-8 H) and 7.04 (ABq, 2H, J = 9 Hz, ics = 10 Hz, C-2' and C-3' H).

In accordance with the above procedure, but where in place of 8-methoxyberberine phenol betaine there is utilized any of the other 8-alkoxyberberine phenol betaines produced in Example II, there are obtained the corresponding dehydronorhydrastine alkyl esters.

In accordance with the foregoing procedures, but starting with any of the 8-alkoxynorcoralydine phenyl betaines, 8-alkoxypalmatine phenol betaines, 8-alkoxyberberubine phenol betaines, and 8-alkoxy-2,3,10-trimethoxyprotoberberine phenol betaines, there are obtained the corresponding 1-(6'-carboalkoxy-4',3'-dimethoxy)-α-hydroxybenzylidene)-6,7-methylenedioxy-1,2,3,4-tetrahydroisoquinolines 1-(6'-carboalkoxy-4',5'-dimethoxy-α-hydroxybenzylidene)-6,7-dimethoxy-1,2,3,4-tetrahydroisoquinolines, 1-(6'-carboalkoxy-5'-hydroxy-4'-methoxy-α-hydroxybenzylidene)-6,7-methylenedioxy-1,2,3,4-tetrahydroisoquinoline and 1-(6'-carboalkoxy-4'-hydroxy-3'-methoxy-α-hydroxybenzylidene)-6,7-dimethoxy-1,2,3,4-tetrahydroisoquinolines respectively.

EXAMPLE IV

N-METHYLATION OF DEHYDRONORHYDRASTINE METHYL ESTER (4) TO DEHYDROHYDRASTINE METHYL ESTER (5)

Dehydrohydrastine methyl ester (4) hydrochloride (0.6 g, 1.2 mmol) was slurried in water 50 ml, neutralized with a solution of aqueous saturated sodium bicarbonate, and extracted with chloroform. The organic layer was filtered through anhydrous sodium sulfate and the solvents removed in vacuo to yield an oil. A solution of the oily free base of (4) (0.49 g 1.2 mmol)) in acetonitrile (100 ml) and methyl iodide (6 ml) was heated under reflux for 8 hours, cooled, and the solvent evaporated to leave a crystalline mass. Recrystallization from methanol ether gave dehydrohydrastine methyl ester (5) (0.5 g (0.926 mmol)) as an orange-yellow hydroiodide salt, mp. 167°–168° C, Anal. Hydroiodide salt. Found: C, 48.84; H, 4.23; I, 23.08. Calc'd. for $C_{22}H_{23}NO_7.HI$: C, 48.81; H, 4.46; I, 23.44%.

Treatment of the salt with aqueous sodium bicarbonate followed by chloroform extraction and evaporation of the solution yields the free base of (5), mp 125°–127° (prisms from methanol). Spectral values for the free base of (5): λmax (in EtOH) 258, 298, 302 and 387 nm (log 4.61, 4.70, 4.68 and 3.92), λmax (in $CHCl_3$ 1670 and 1735 $cm^{-1}$, nmr δ2.22 (s, 3H, N-$CH_3$), 2.5–3.4 (m, 4H, $CH_2$—$CH_2$), 3.45 (s, 1H, C-1 H), 3.81, 3.83 and 3.97 (3s, 3×3H, 3 $OCH_3$), 5.83 (s, 2H, $OCH_2O$), 6.32 and 6.60 (2s, 2×1H, C-8 and C-5 H), and 7.30 (ABq, 2H, J = 9 Hz, ics = 74 Hz, C-3' and C-2' H).

In accordance with the above procedures, but where, in place of methyl iodide there is utilized methyl chloride, methyl bromide, dimethyl sulfate, trimethyloxoniumfluoroborate or trimethyl phosphate, there is obtained the same product. Similarly, when there is utilized ethyl iodide, n-propyl bromide, bromobenzene and benzyl bromide, there are obtained the corresponding N-ethyl, N-n-propyl, N-phenyl and N-benzyldehydronorhydrastine methyl esters (5).

In accordance with the foregoing procedures, but starting with any of the other dehydronorhydrastine alkyl esters prepared in accordance with Example III, there are obtained the corresponding N-alkyl, N-phenyl or N-phenylalkyldehydronorhydrastine alkyl esters (5).

In accordance with the foregoing procedures, but starting with any of the carboalkoxyhydroxybenzylidenetetrahydroisoquinolines prepared in Example II, there are obtained the corresponding N-alkyl or N-phenyl or N-phenylalkyl derivatives (5).

EXAMPLE V

CONVERSION OF DEHYDROHYDRASTINE METHYL ESTER (5) HYDROIODIDE TO (+)-α-HYDRASTINE AND (+)-β-HYDRASTINE (6-a AND 6-b)

A solution of dehydrohydrastine methyl ester (5) hydroiodide (0.8 g, 1.5 mmol) in ethanol (50 ml) was reduced with excess sodium borohydride at room temperature and after decolorization the solution was allowed to stir an additional four hours. The reaction mixture was neutralized and acidified with aqueous hydrochloric acid, and allowed to stand for three hours. After neutralization with solid sodium bicarbonate, the solution was partitioned with chloroform, and the chloroform extracts dried over anhydrous sodium sulfate, and filtered. The solvent was evaporated to give a residue which crystallized from methanol. The crystals, 0.55 g, were a mixture of (+)-α-(+)-β-hydrastine, in a ratio of approximately 1:2. Column chromatography on silica gel using chloroform/methanol mixtures afforded (+)-β-hydrastine (6a-), 0.18 g (0.47 mmol), and (+)-β-hydrastine (6b-), 0.36 g (0.93 mmol), identical in all respects with semi-synthetic and authentic samples of (−)-α-hydrastine and (−)-β-hydrastine, respectively.

In accordance with the above procedure, but where, in place of dehydrohydrastine methyl ester, there is employed as starting material any of the dehydrohydrastine alkyl esters (i.e., N-methyldehydronorhydrastine alkyl esters) in the form of their hydrohalides, there is obtained the same mixture of α- and β-hydrastine. Similarly, where the other N-substituted-dehydronorhydrastine alkyl esters are employed, the corresponding α- and β-N-substituted nordehydrohydrastines are produced.

In accordance with the above procedure, but where starting with any of the N-substituted carboalkoxy α-hydroxy-benzylidenetetrahydroisoquinolines prepared in accordance with Example IV, there is obtained the corresponding N-substituted phthalideisoquinolines.

EXAMPLE VI

PREPARATION OF INTERMEDIATE (7) (RED FILTRATE)

A filtered solution of 0.5 g (0.7 mmol) of dimer (2) in pyridine (50 ml) was treated with pyridine hydrochloride (1 g), and the solution stirred at room temperature for two hours. The crystalline precipitate of berberine (1) chloride was filtered off, and the filtrate was allowed to stand until no further crystallization took place. After a second filtration, about 50 ml of a red pyridine solution (7) was obtained, as well as an accumulated total of 0.2 g (0.5 mmol, 79% yield), of crystalline berberine chloride.

In accordance with the above procedures, but starting with the dimers obtained in Example I, there was provided similar solutions together with the corresponding salts of starting material (berberine or protoberberines) (1).

EXAMPLE VII

PREPARATION OF 2,3-METHYLENEDIOXY-9,10-DIMETHOXY-8,13-DIOXO-14-HYDROXY BERBERINE (8)

The red filtrate (7) obtained in Example VI was poured onto 200 g ice and 20% HCl (50 ml) to form a violet-black suspension. The resulting mixture was diluted with 200 ml cold water to colorlessness and extracted with chloroform. The organic layer was dried over anhydrous potassium carbonate, the solvent removed in vacuo, and the residue was purified by column chromatography on silica gel using chloroform as the eluent to afford (8) as a colorless oil. Crystallization from ether gave 0.15 g (0.4 mmol), 58% yield, of 2,3-methylenedioxy-9,10-dimethoxy-8,13-dioxo-14-hydroxyberberine (8) as colorless rosettes of needles, mp. 134° C. High resolution mass spectrum, M+; found m/e 383.; calcd for $C_{20}H_{17}NO_7$ 383. IR $\nu$ max (in $CHCl_3$) 1720, 1670, 1580 and 1485 cm$^{-1}$. Mass spectrum: m/e 383, 367, 338, 220, 190, 176 (base), 165, and 148. NMR ($\delta$, $CDCl_3$, 60 MHz) 2.6–3.0 (m, 2H), 3.88 (s, 3H), 3.92 (s, 3H), 4.4–5.0 (m, 2H), 5.88 (s, 2H), 6.53 (s, 1H), 7.10 (d, 1H, J = 8.5 Hz) and 7.74 (d, 1H, J = 8.5 Hz).

In accordance with the above procedure, but starting with the red filtrates (7) from the dimers of nocoralydinium, palmatinium, berberubinium and 2,3,10-trimethoxy-11-hydroprotoberberinium chlorides in accordance with Examples I and VII, there are obtained 2,3,10,11-tetramethoxy-8,13-dioxo-14-hydroxyberbine, 2,3-methylenedioxy-9,14-dihydroxy-10-methoxy-8,13-dioxoberbine and 2,3,10-trimethoxy-11,14-dihydroxy-8,13-dioxoberbine.

EXAMPLE VIII

PREPARATION OF 2,3-METHYLENEDIOXY-9,10,14-TRIMETHOXY-8,13-DIOXOBERBINE (9)

(a) The red filtrate (7) obtained in Example VI was diluted with 200 ml of methanol, and the solvent evaporated at 40° in vacuo. Reevaporation with two other aliquots of 200 ml each of methanol gave a dark brown residue which was rapidly passed through a short silica gel column using 3% methanol in chloroform as eluent to yield (9) (0.23 g 0.58 mmol) as a colorless oil. Crystallization from ether furnished 2,3-methylenedioxy-9,10,14-trimethoxy-8,13-dioxoberbine (9) 0.18 g (0.45 mmol, 67% yield), as colorless rosettes of fine needles, mp. 126° C.

Elemental anal. by high resolution mass spec.: M+, found: m/e 397.1196; calcd for $C_{21}H_{19}NO_7$: 397.1160. Mass spectrum: m/e 397, 382, 366, 338, 324, 322, 223, 208, 193, 191 and 175. IR $\nu$ max (in $CHCl_3$) 1725, 1665, 1585 and 1485. NMR ($\delta$, $CDCl_3$, 60 MHz): 2.80 (m, 2H), 3.17 (s, 3H), 3.95 (s, 3H), 3.98 (s, 3H), 5.00 (m, 2H), 5.92 (s, 2H), 6.62 (s, 1H), 6.98 (s, 1H), 7.11 (d, 1H, J = 8 Hz), and 7.74 (d, 1H, J = 8 Hz).

Compound (9) characteristically turns deep violet upon exposure to strong mineral acid; with no heat being required.

In accordance with the above procedure, but where in place of methanol there is used ethanol, propanol, butanol, ethyl mercaptan, acetic acid, propionic acid, or benzoic acid there are obtained the corresponding 14-ethyl, 14-propyl, 14-butyl, 14-ethylthio, 14-acetoxy, 14-propionoxy or 14-benzoyloxy-2,3-methylenedioxy-9,10-dimethoxy-8,13-dioxoberbines respectively.

In accordance with the above procedure, but starting with the red filtrates (7) from dimers of nor-coralydinium, palmatinium, berberubinium, and 2,3,10-trimethoxy-11-hydroprotoberberinium chlorides prepared in accordance with Examples I and VII, there is obtained the corresponding 14-methyl, 14-ethyl, 14-propyl, 14-butyl, 14-ethylthio, 14-acetoxy, 14-propionoxy, 14-benzoyloxy-2,3,10,11-tetramethoxy-8,13-dioxoberbine; 2,3,9,10-tetramethoxy-8,13-dioxoberbine; 2,3,9,10-tetramethoxy-8,13-dioxoberbine; 2,3-methylenedioxy-9-hydroxy-10-methoxy-8,13-dioxoberbine and 2,3,10-trimethoxy-11-hydroxy-8,13-dioxoberbines, respectively.

(b) Starting with any of the products of Example VII, any of the corresponding foregoing compounds (9) may be obtained in the following manner. The appropriate compound (9) (600 mg, 1.6 mm) is taken up in dilute, cold (ca 5° C) hydrochloric acid (5% w/v, 200 ml). There is added an excess of the nucleophile — i.e., methanol, ethanol, propanol, butanol, ethyl mercaptan, acetic acid, propionic acid, butyric acid or benzoic acid and the mixture agitated until all color had substantially disappeared. The product is then isolated in accordance with the procedures of Example VII supra to yield the desired corresponding product.

EXAMPLE IX

13-METHOXYOXYBERBERINE (10)

A methanolic solution of 2,3-methylenedioxy-9,10,14-trimethoxy-8,13-dioxoberbine (9) (0.4 g, 1 mmol) was stirred with an excess of sodium borohydride and the mixture allowed to stir at room temperature overnight. After evaporation of the solvent in vacuo, the residue was rapidly partitioned between chloroform and water at pH 7, and the organic layer was then dried over anhydrous potassium carbonate. The solvent was decanted and evaporated, and the residue dissolved in scrupulously pure and anhydrous tetrahydrofuran which had been freshly distilled. To this tetrahydrofuran solution was added methyl iodide (2 ml) and sodium hydride (350 mg) (50:50 in oil dispersion). The reaction mixture was heated under reflux for one hour, and then allowed to stand for 12 hours. The mixture was poured into aqueous hydrochloric acid (20 ml, 10%) and stirred for 20 minutes, then extracted with chloroform. The organic layer was evaporated to dryness, and the residue crystallized from methanol to yield 13-methoxyoxyberberine (10) (0.3 g, 0.8 mmol, 79%), as light tan prisms, mp 193–194.

EXAMPLE X

CONVERSION OF OXYBISBERBERINE (2) TO 13METHOXYOXYBERBERINE (10)

To a slurry of oxybisberberine (2) (0.5 g, 9.7 mmol) in benzene (30 ml), was added 3 ml of dimethyl sulfate, and the slurry heated to 50° C for three hours. After standing overnight, a saturated solution of aqueous sodium bicarbonate (10 ml) was added, stirred for one hour, and the resulting mixture partitioned between chloroform and the aqueous layer. The chloroform layer was decolorized with Norit, dried over anhydrous potassium carbonate, and filtered. The residue after evaporation of the solvent was flushed through a short silica gel column using chloroform as solvent, and the major blue-white fluorescent band (under 254 nm uv light) was isolated and crystallized from methanol to furnish 13-methoxyoxyberberine (10) 0.18 g (0.48 mmol), 70% yield, as light tan prisms, mp. 194°–195° C. Mass spectrum m/e 381 and 366. IR $\nu$ max (in CHCl$_3$) 1650 and 1600 cm$^{-1}$, NMR ($\delta$, CDCl$_3$, 60 MHz) 2.82 (t, J = 7 Hz, 2H), 3.55 (s, 3H), 3.92 (s, 3H), 3.98 (s, 3H), 4.23 (t, J = 7 Hz, 2H), 5.93 (s, 2H), 6.68 (s, 1H), 7.48 (ABq. J = 9 Hz, ics = 16 Hz, 2H), and 7.90 (s, 1H).

EXAMPLE XI

CONVERSION OF 8-METHOXYBERBERINE PHENOL BETAINE (3) to 13-METHOXYOXYBERBERINE (10)

To a stirred solution of 8-methoxyberberine phenol betaine (1.5 g, 3.9 mmol) in refluxing tetrahydrofuran was added methyl iodide (6 ml) and heating under reflux was continued for 4 hours, whereupon the initial red color had become yellow-orange. After removal of the solvent in vacuo, the residue crystallized from methanol. Two recrystallizations from methanol yielded 13-methoxyoxyberberine 1.3 g (3.4 mmol), 87% yield, as light tan prisms, mp. 194°–195° C.

We claim:

1. A process for the oxidative dimerization of a compound selected from the group of berberinium and protoberberinium derivatives, free of oxoberberine or the corresponding oxoprotoberberine derivatives comprising the steps of (a) reacting a compound having the formula

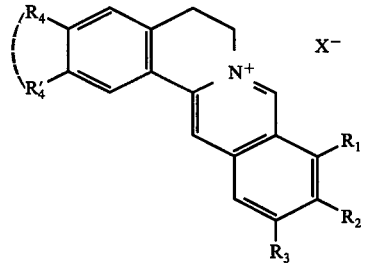

wherein R$_1$, R$_2$, and R$_3$ are hydrogen, hydroxy, alkanoyloxy, alkoxy, phenylalkanoyloxy, phenylalkoxy, alkoxyalkoxy, cycloalkylalkoxy, alkoxycarbonyloxy, phenylalkoxycarbonyloxy, R$_4$ and R$_4'$ have the same value as R$_1$ other than hydrogen and hydroxy, and, when joined together R$_4$ and R$_4'$ form a member of the group consisting of alkylenedioxy, alkylenedicarbonyloxy, phenylalkylenedicarbonyloxy, diphenylalkylenedicarbonyloxy, phenylalkylenedioxy, diphenylalkylenedioxy, alkoxyalkylenedioxy, cycloalkylalkylenedioxy, alkylenedioxydicarbonyloxy, phenylalkylenedioxydicarbonyloxy, diphenylalkylenedioxydicarbonyloxy, in all of the foregoing groupings the prefix alk . . . signifies a carbon and hydrogen containing moiety of 1 to 5 carbon atoms, provided, however, that cycloalkyl is 3 to 7 carbon atoms; X$^-$ is an anion of an organic or inorganic acid capable of quaternizing the berberinium, or protoberberinium group with an oxidizing agent having an anion selected from the group consisting of ferric ions and ferricyanide in the presence of an aqueous inorganic hydroxylic base selected from the group consisting of ammonium hydroxide, alkali metal hydroxide, and alkaline earth metal hydroxide;

(b) extracting the product from the reaction mixture with a substantially water immiscible reaction inert polar organic solvent, substantially immediately, to form a dimer of said compound.

2. A process according to claim 1 wherein the base is selected from the group consisting of aqueous potassium hydroxide, aqueous sodium hydroxide, aqueous calcium hydroxide and aqueous barium hydroxide, and the oxidant is selected from the group consisting of potassium ferricyanide, sodium ferricyanide, ammonium ferricyanide, ferric chloride, and ferric nitrate and X is a member selected from the group of cations consisting of chloride, bromide, iodide, nitrate, hydrogen sulfate, sulfate, acetate, and oxalate.

3. A process according to claim 1 comprising the steps of
   (a) mixing the berberinium or protoberberinium compound with the oxidant,
   (b) adding the base, and
   (c) mixing the reaction mixture and extracting the reaction product substantially immediately.

4. A process according to claim 5 comprising commencing the extracting of the reaction product from the reaction mixture loss than ten minutes after the addition of the aqueous hydroxide.

5. A process according to claim 1 wherein
   $R_1$, $R_2$, and $R_3$ are selected from the group consisting of acetoxy, methoxy, benzoyloxy, benzyloxy, methoxymethoxy, cyclopropylmethoxy, ethoxycarbonyloxy, benzoyloxycarbonyloxy, hydroxy, and hydrogen,
   $R_4$ and $R_4'$ have the same values as $R_1$ other than hydrogen and hydroxy and when joined together form a member selected from the group consisting of methylenedioxy, ethylenedioxy, oxacyl, malonyl, succinyl, α-carboxybenzoyl, 1,2-diphenylsuccinyl, 1-phenylethylenedioxy, 1,2-diphenylethylenedioxy, methoxymethylenedioxy, cyclopropylmethylenedioxy, ethylenedioxydicarbonyloxy, 1-phenylethylenedioxy, 1,2-diphenylethylenedioxy, methoxymethylenedioxy, cyclopropylmethylenedioxy, ethylenedioxydicarbonyloxy, 1-phenylethylenedioxydicarbonyloxy, 1,2-diphenylethylenedioxydicarbonyloxy, and $X^-$ is selected from the group consisting of chloride, bromide, iodide, hydrogen sulfate, sulfate, nitrate, acetate, benzoate, and oxalate.

6. A process according to claim 1 wherein $R_1$ is methoxy, $R_2$ is methoxy, $R_3$ is hydrogen, and $R_4$ and $R_4'$ are joined together to form methylenedioxy, the base is an aqueous alkali metal hydroxide and the oxidant is a ferricyanide.

7. Oxybisberine being the dimerization product of the basic oxidation of berberine having the following characteristics M.P. 215°–216° C, molecular weight between 715 and 736,
   elemental analysis C, 66.13 ± 0.21; H, 5.15 ± 0.25; N, 3.90 ± 0.10 and residual O;
   an infrared spectrum devoid of carbonyl absorption bands,
   NMR (pyridine-$d_5$ at 60 MHz with TMS as internal standard):
   $\delta$2.00–3.40 m (8H); 3.47 s (3H); 3.57 s (3H); 3.88 s (3H); 3.93 s (3H); 4.58 m (1H); 5.28 s (1H); 5.60 s (2H); 5.67 m (1H); 5.75 m ABq (2H); 6.27, 6.44, 6.48, 6.58, 6.63, and 6.78: (8H in all) (some overlap of peaks); 7.68 s (1H), Crystallographic characteristic (monoclinic plates from pyridine-ether) space group P2$_1$/C, cell dimensions A = 16.12, B = 11.19, C = 16.91, and $\beta$ = 118° 05'.

* * * * *